(12) United States Patent
Suda

(10) Patent No.: US 6,229,318 B1
(45) Date of Patent: May 8, 2001

(54) ELECTRICAL RESISTANCE TYPE HUMIDITY SENSOR

(75) Inventor: Toshikazu Suda, Yokohama (JP)

(73) Assignees: Suda Toshikazu, Kanagawa-Ken; Sanriki Kogyo Kabushiki Kaisha, Tokyo, both of (JP)

(*) Notice: Subject to any disclaimer, the term of this patent is extended or adjusted under 35 U.S.C. 154(b) by 0 days.

(21) Appl. No.: 09/007,366

(22) Filed: Jan. 15, 1998

(30) Foreign Application Priority Data

Feb. 25, 1997 (JP) .................................................. 9-056968

(51) Int. Cl.$^7$ .................................................. G01N 27/04
(52) U.S. Cl. ........................................... 324/696; 324/694
(58) Field of Search ........................... 324/694, 696, 324/713, 715, 721, 722, 724

(56) References Cited

U.S. PATENT DOCUMENTS

| 3,705,375 | 12/1972 | Hershler . | |
|---|---|---|---|
| 4,489,603 | 12/1984 | Fukami et al. . | |
| 4,594,569 | * 6/1986 | Fukushima et al. | 338/35 |
| 4,649,364 | 3/1987 | Tanahashi et al. . | |
| 4,658,120 | * 4/1987 | Fujikawa | 219/505 |
| 4,717,811 | * 1/1988 | Fujii | 219/497 |
| 5,027,077 | * 6/1991 | Ynangisawa et al. | 324/712 |
| 5,345,184 | * 9/1994 | Andoh | 324/720 |

FOREIGN PATENT DOCUMENTS

| 0 186 039 | 7/1986 | (EP) . |
|---|---|---|
| 1364672 | 5/1964 | (FR) . |
| 2 760 092 | 2/2000 | (FR) . |
| 2 158 246 | 11/1985 | (GB) . |
| 2 332 452 | 3/1999 | (GB) . |
| 58-72046 | 4/1983 | (JP) . |
| 61-112953 | 5/1986 | (JP) . |

* cited by examiner

Primary Examiner—Safet Metjahic
Assistant Examiner—Jose M. Solis
(74) Attorney, Agent, or Firm—Arent Fox Kintner Plotkin & Kahn, PLLC

(57) ABSTRACT

An electrical resistance type humidity sensor is herein disclosed which comprises a humidity sensor in which electrodes are formed on a woodceramics substrate having linear characteristics with humidity, and a temperature sensor for temperature correction in which electrodes are formed on other woodceramics substrate having the identical characteristics as in the woodceramics humidity sensor and a film coating of a nonhygroscopic material is formed on the surface of the substrate. Thus, a resistance value measured by the woodceramics humidity sensor is corrected on the basis of a resistance value measured by the woodceramics temperature sensor to obtain an output voltage in proportion to a relative humidity. A structure insensitive to a humidity formed from all the same material i.e. woodceramics as in the humidity sensor is utilized as the temperature sensor for the temperature correction to carry out the temperature correction by the temperature sensor, whereby the humidity sensor having the linear characteristics can be obtained.

5 Claims, 4 Drawing Sheets

ELECTRICAL RESISTANCE TYPE HUMIDITY SENSOR

BACKGROUND OF THE INVENTION

1. Field of the Invention

The present invention relates to humidity sensor for detecting humidity, and more specifically, it relates to an electrical resistance type humidity sensor which uses woodceramics and which is inexpensive, small, excellent in heat resistance, and with high accuracy.

2. Description of the Related Art

Humidity sensors can be used not only to measure a humidity in an atmosphere but also to automatically control humidifiers, dehumidifiers, air-conditioners for humidity adjustment and the like. For these humidity sensors, various materials are used, but in recent years, humidity sensors using ceramics are known. When a certain voltage is applied to the ceramics humidity sensor, an electrical resistance exponentially alters with a relative humidity, whereby a value of the relative humidity can be detected on the basis of the electrical resistance. However, the usual ceramic humidity sensor has the following problem. That is to say, in the ceramics humidity sensor, an electrically insulating material is used, so that an impedance is very high. In the case of the ceramic humidity sensor, the impedance becomes significantly high especially in a low humidity range, and hence, by an ordinary method, the measurement of the humidity is difficult, and an electronic circuit undergoes also complexity.

Moreover, most of the ceramic humidity sensors have non-linear characteristics, and actually, a change in humidity-resistance characteristics does not comply with a completely exponential function and is curved. For this reason, when a measurement range is expanded, a measurement error increases, so that an output with high accuracy can not be obtained. In addition, because a linearizing circuit for correcting the curvature is not complete, the circuit itself is fairly complex, which is a large obstacle in practice. Furthermore, the ceramic humidity sensors depend on temperature, and even if the humidity is constant, the electrical resistance of the ceramic sensors inconveniently changes owing to the temperature. In addition, temperature coefficients of a thermistor and a platinum temperature measuring elements for use in the usual temperature measurement are different from temperature coefficients of the ceramics humidity sensors, and hence, there is also a significant problem that temperature correction cannot completely be accomplished.

Humidity sensors have been suggested which are equipped with a temperature sensor for the temperature correction which can correct the temperature dependence of such a ceramics humidity sensor. For example, there are "a humidity detection circuit" described in Japanese Patent Application Laid-open No. 274251/1987 and "a ceramics humidity sensor" described in Japanese Patent Publication No. 81974/1995. The former "humidity detection circuit" is constituted as follows. At an end of the humidity sensor which has characteristics of changing in impedance according to the changes in humidity and temperature, where an oscillation circuit is connected and at the other end of the said humidity sensor, a temperature correction element which has the same thermistor coefficient with said humidity sensor and where impedance changes according to changes in temperature, is connected. Furthermore, a rectification circuit and an amplifier circuit which process as required humidity detection signals at a contact point of said humidity sensor and said temperature correction element, are also connected. Said detection signals or processed detection signals are input into the first input terminal and proper reference signals are input into the second input terminal. Then, a comparator circuit where comparison of the values between said reference signals and said detection signals are made, is connected. Also, an output circuit which outputs the humidity signal by receiving output from said comparator circuit is connected.

However, in the case of the above "humidity detection circuit", an oscillation circuit is used and the temperature correction element connected at the other end of the humidity sensor should have the same thermistor coefficient with the humidity sensor and also changes impedance according to the changes in temperatures. However, since the humidity sensor and the temperature sensor are different in materials, we suffer a significant problem that it is difficult to manufacture both of them so that they may have identical characteristics.

Moreover, the above "ceramics humidity sensor" is provided with an fine ceramics substrate having a high dielectric constant, a porous ceramics layer having a high dielectric constant formed on a part of one surface of the substrate, a mesh-like measurement electrode formed on the said porous ceramics layer, a reference electrode formed on a part where the porous ceramics layer is not formed, a common electrode formed on the other side of the said ceramics substrate, and an arithmetic unit which measures an electrostatic capacitance between the measurement electrode and the common electrode as well as an electrostatic capacitance between the reference electrode and the common electrode and which calculates the obtained results. By taking such a constitution, temperature correction becomes possible.

However, in the case of the above "ceramics humidity sensor", it becomes highly complicated in manufacture to form on the ceramics substrate a porous layer, a measurement electrode, a reference electrode and also a common electrode as well as a guard electrode. There is also a problem that signal process by the arithmetic unit becomes complicated.

SUMMARY OF THE INVENTION

Therefore, an object of the present invention is to provide an electrical resistance type humidity sensor which does not have defects of conventional humidity sensors and which is highly accurate in the wide range of humidity and which has a simple constitution by using woodceramics whose humidity-resistance characteristics are excellently linear as opposed to the non-linear characteristics of other sensor materials.

Another object of the present invention is to provide an electrical resistance type humidity sensor which is excellent in both reliability and mass-production.

Still another object of the present invention is to provide an electrical resistance type humidity sensor which can be manufactured simply and at a low cost.

BRIEF DESCRIPTION OF THE DRAWINGS

The above-mentioned various objects and benefits of the present invention will be fully understood by considering the following description and drawings attached thereto.

DESCRIPTION OF THE PREFERRED EMBODIMENT

Figure 1:
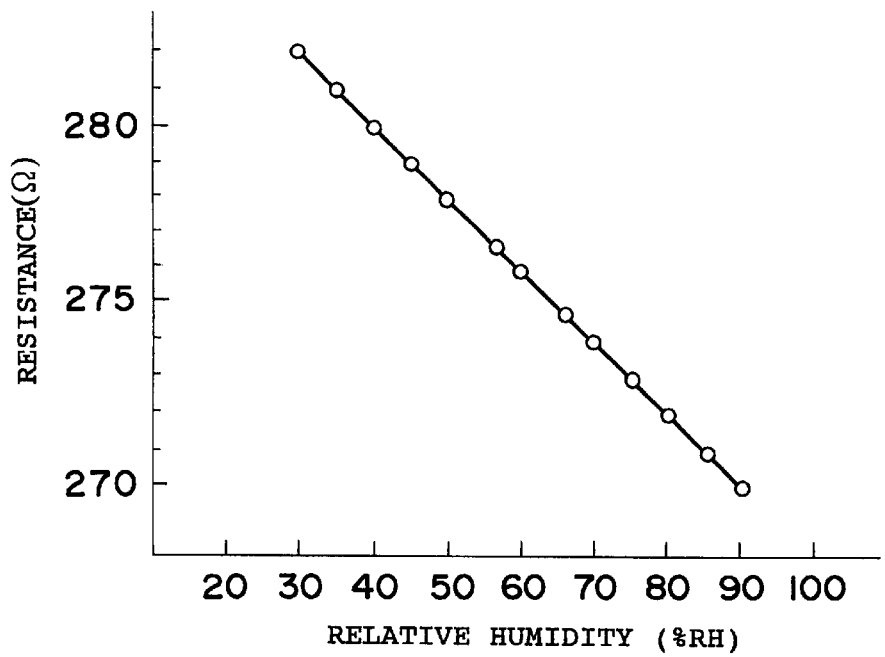
FIG. 1 is a relative humidity-electrical resistance characteristics of an electrical resistance type humidity sensor regarding the present invention.

In order to achieve the above objects, the present invention is constituted as follows. That is to say, an electrical resistance type humidity sensor regarding the present invention comprises a humidity sensor in which electrodes are formed on a woodceramics substrate, and a temperature sensor for temperature correction in which electrodes are formed on other woodceramics substrate having the identical characteristics as in the woodceramics used for humidity sensing and a film coating of a nonhygroscopic material is formed on the surface of the substrate. Thus, resistance values measured by the humidity sensor are corrected on the basis of resistance values measured by the temperature sensor having the same temperature coefficient as in the humidity sensor to obtain an output voltage in proportion to a relative humidity.

The humidity sensor regarding the present invention is constituted so as to use woodceramics of the only material with linear characteristics to humidity and, with the surface sealed the other woodceramics make into a humidity non-sensitive structure, acting as a temperature sensor for temperature correction, and employs woodceramics of the same temperature coefficient for the temperature correction object. Accordingly, a wide range of humidities can be measured in highly accurate and highly reliable manner. Furthermore, being simple in structure, it is excellent in mass production, low in price and possible to be made small in size. In addition, by making a temperature correction with the woodceramics of the identical material, the temperature coefficient can be kept identical so that the electronic circuit can be simplified to a large extent. Moreover, having a proper degree of electrical resistance (being not insulator), causes woodceramics to be employed as self-heating element. Letting electric current flow through woodceramics can perform a heat-cleaning, because it is of the electrical resistance type. That is to say, a heating operation can be done by letting electric current flow higher than at the time when humidity is measured. Through the heating operation, heat is generated and moisture in the woodceramics humidity sensor can be evaporated in a short period of time. After the heating operation, letting flow the low electric current causes the ordinary measurement for the humidity detection object. Thus, the electrical resistance type humidity sensor using the woodceramics does not become moldy, in contrast to other humidity sensors in which, for example, polymers, celluloses, ceramics, hairs and the like are used.

Moreover, an electrical resistance type humidity sensor regarding the present invention is a sensor wherein electrodes are formed at both ends and the center of one woodceramics substrate; a film coating of a nonhygroscopic material is formed on the surface between the electrode at one end and the common electrode at the center; a film-free portion between the electrode at the other end and the common electrode at the center functions as a humidity sensor; and a portion having the film coating functions as a temperature sensor for temperature correction. Furthermore, in the above electrical resistance type humidity sensor having the above constitution according to the present invention, one woodceramics substrate may be formed in a line-shaped form, or one woodceramics substrate may be formed in a U-shaped form. In the case that one woodceramics substrate is used in this way, a manufacturing process can be simplified and a structure can be miniaturized.

Furthermore, an electrical resistance type humidity sensor regarding the present invention is a sensor wherein two thin plates or thin films coating of woodceramics are formed on one insulating substrate; a film of a nonhygroscopic material is formed on one surface thereof as a temperature sensor for temperature correction; any film is not formed on the other surface thereof and the film-free surface functions as a humidity sensor; and a resistance value measured by the humidity sensor is corrected on the basis of a resistance value measured by the temperature sensor to obtain an output voltage in proportion to a relative humidity.

For a more understanding, the present invention will be described in more detail in accordance with embodiments shown in drawings.

Here, woodceramics which can be used in the present invention means a porous carbon material which is obtained by sintering and carbonizing a composite material of a woody material (lumber, paper or the like) and a thermosetting resin at a high temperature. The woodceramics are also made of raw materials such as waste woods and waste papers (used papers), and so they are ecomaterials which are kind to the earth. It is known that carbon materials are good conductors of electricity, and their electrical resistivities depend on temperature. The electrical resistance of woodceramics depends also on the temperature, and FIG. 2 and FIG. 3 show the measured values regarding the above characteristics.

FIG. 1 shows the measured values of relative humidity-resistance characteristics in response to humidity change under the condition where a direct current of 5 mA is passed while an atmospheric temperature is kept at 26° C. The woodceramics which has been employed herein, has been prepared by using a medium density fiberboard(MDF) as a kind of woody material, ultrasonically impregnating the MDF board with a phenolic resin as the thermosetting resin, and then sintering the subsequent material at 750° C. In the general ceramics, an electrical resistance exponentially changes with relative humidity (% RH) and has a curved non-linearity. However, as is apparent from the results of the measurement, the woodceramics have linear characteristics to the relative humidity (% RH), and it can be recognized that a highly precise measurement is possible in a wide range of the humidity. Since the usual ceramics are insulators, impedance values particularly become high at low humidity, so that the measurement is significantly difficult.

Figure 2:
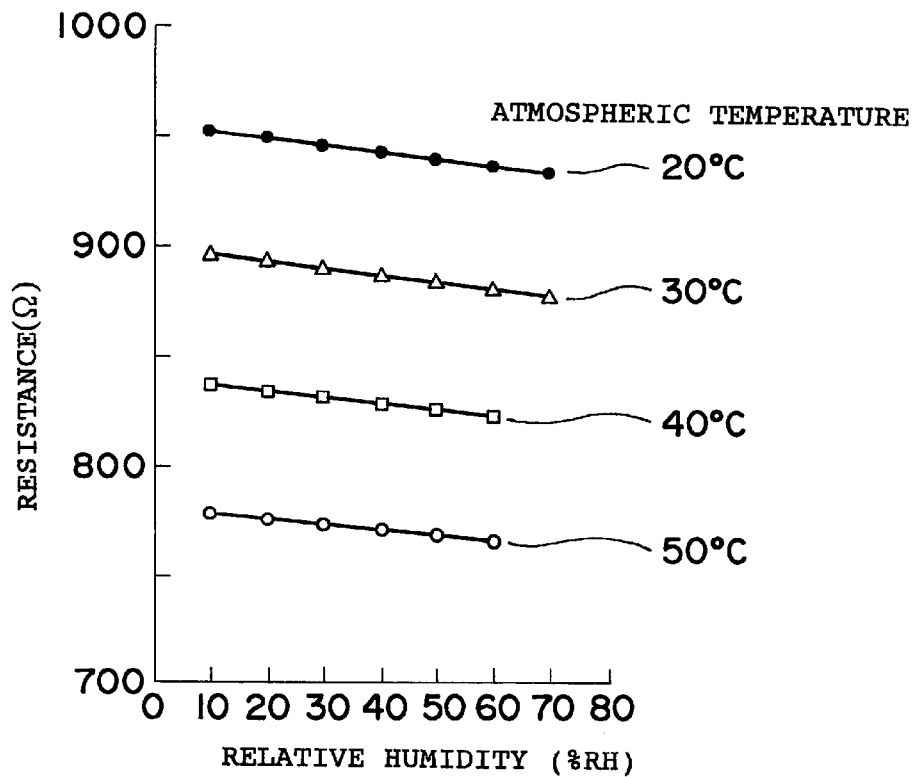
FIG. 2 is a similar humidity-resistance characteristics.
Figure 3:
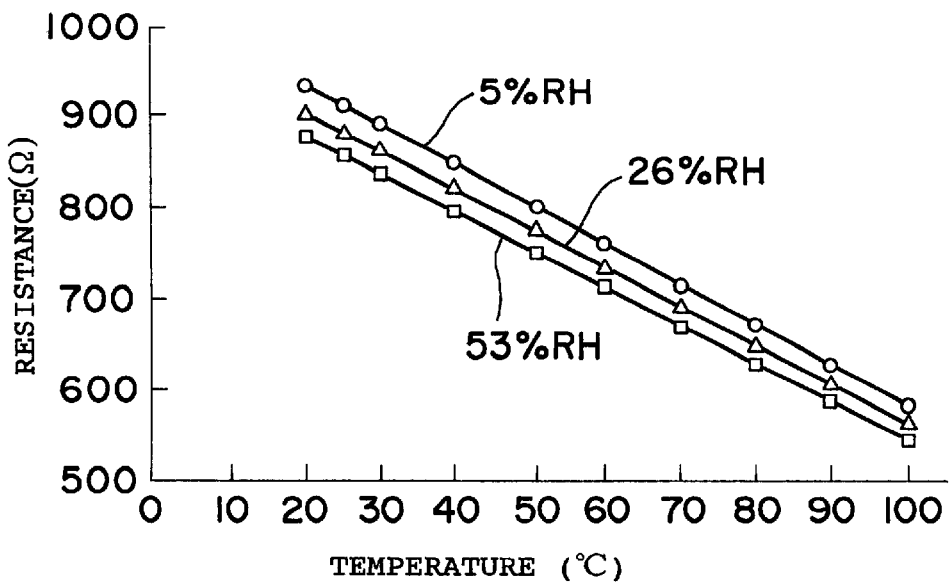
FIG. 3 is a temperature-resistance characteristics.

FIG. 2 shows the relative humidity-resistance characteristics of another woodceramics sample sintered at 650° C. and measured at a constant DC current of 1 mA, changing the atmospheric temperatures as parameters to 20° C., 30°

C., 40° C. and 50° C. Note that the electrical resistance of the usual ceramics has non-linear characteristics to the relative humidity, whereas the electrical resistance of the woodceramics has excellently linear characteristics to the relative humidity. It can be recognized from this fact that by utilizing woodceramics the highly precise measurement is possible in a wide range of humidities.

FIG. 3 shows temperature-resistance characteristics measured in compliance with the change of the temperature (° C.) at a constant DC current of 1 mA, while the relative humidities (% RH) are maintained at 5% RH, 26% RH and 53% RH, respectively. The woodceramics which has been employed herein, has been prepared by using a medium density fiberboard(MDF) as a kind of woody material, ultrasonically impregnating the MDF board with a phenolic resin as the thermosetting resin, and then sintering the subsequent material at 650° C. As is apparent from the measured results, in contrast to the usual ceramics, the woodceramics have linear characteristics with respect to the temperature, and it can be recognized that a highly precise temperature measurement is possible in a wide range of temperatures. When the usual ceramics are used for the temperature measurement, an impedance value particularly becomes high, so that the measurement at low temperatures becomes significantly difficult.

As described above, in the present invention, the linear characteristics of the woodceramics to both humidity and temperature are utilized, and the humidity sensor and the temperature sensor for the temperature correction are made of one material, that is, woodceramics.

Consequently, since the same material woodceramics having the identical characteristics are used as the humidity sensor and the temperature sensor, temperature coefficients thereof are the same. Therefore, when the humidity is read, the temperature correction can be accomplished very simply and with high accuracy.

In the electronic humidity measurement, almost all the humidity sensitive elements have temperature dependence, and therefore, in order to find out the accurate humidity, it is necessary that the temperature is measured at the same time and a temperature contribution should be then subtracted therefrom. Usually, in order to make the temperature correction, a thermistor, a platinum temperature measuring element or the like is generally employed for temperature measurement. However, they are different in material from the humidity sensor, and in the case of them, the temperature coefficients are largely different each other, and hence an output processing circuit of the humidity sensor and an output processing circuit of the temperature sensor are specific and complex.

The present invention takes advantage of the fact that the woodceramics have good linear characteristics with respect to both the humidity and the temperature, so that when one of the two has a structure insensitive to humidity, it can easily be used as the temperature sensor for the temperature correction. Naturally, since the other is sensitive to both the temperature and humidity, when the output of "a temperature contribution + a humidity contribution" in the humidity sensor is subtracted by the use of the output of the temperature sensor, the humidity contribution alone is obtained, whereby the relative humidity can easily be found. That is to say, one feature of the present invention is that, by utilizing the identical material, i.e. woodcermics for temperature correction, the processing circuit becomes very simple and easy, moreover highly precise. In addition, in the present invention, since by utilizing the fact that the woodceramics themselves have a moderate resistance, a current can be passed through them, whereby the woodceramics can possess a function as a heater. According to the present invention, the measurement of the humidity can be temporarily stopped to vaporize moisture in woodceramics in a short period of time by this heater function, whereby the sensor can be protected from mold.

Figure 4:
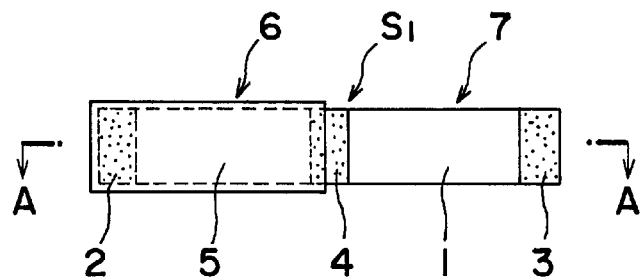
FIG. 4 is a plan view of the first embodiment of the present invention.
Figure 5:
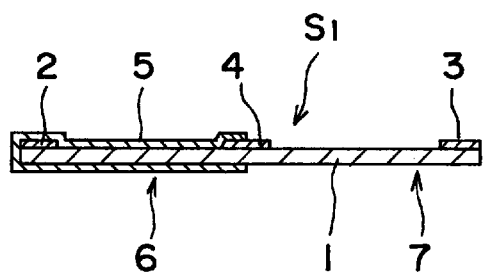
FIG. 5 is a sectional view cut along the A—A line in FIG. 4.

A humidity sensor S1 of the first embodiment which utilizes the woodceramics of the above-mentioned characteristics will be explained. First, to explain about the first embodiment, which is shown in FIG. 4 and FIG. 5, numeral 1 is a woodceramics substrate on which measuring electrodes 2 and 3 are formed at both ends of the above-mentioned woodceramics substrate 1, and a common electrode 4 is formed in the central part. Furthermore, the region which occupies half of the woodceramics substrate 1 between the above-mentioned measuring electrode 2 and the common electrode 4, is entirely sealed by a film coating 5 with a material which does not have hygroscopic property. As a material without hygroscopic property, for example, epoxy resin, unsaturated polyester-type resin, acrylic-type resin, ABS resin, silicone rubber, glass type adhesive and the like may be used. To each of the above-mentioned electrodes, a lead wire is connected. In the above-mentioned configuration, the region between the measuring electrode 2 and the common electrode 4 on which the film coating 5 is formed, is not affected by humidity, gives a temperature sensor 6 for temperature correction, and the region between the measuring electrode 3 and the common electrode 4, on which the coating 5 is not formed, is set up as a humidity sensor 7.

Figure 6:
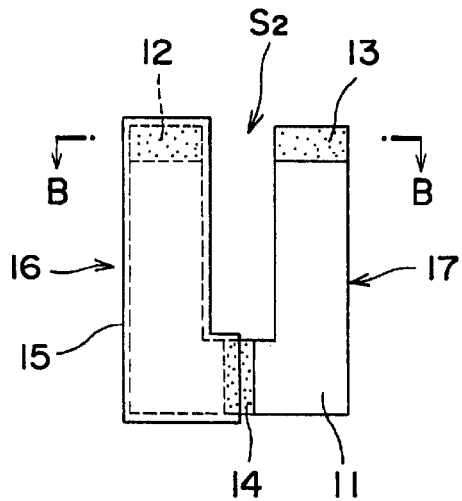
FIG. 6 is a plan view of the second embodiment of the present invention.
Figure 7:
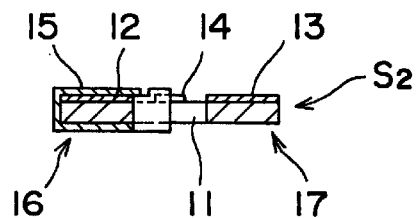
FIG. 7 is a sectional view cut along the B—B line in FIG. 6.

Furthermore, to explain about the humidity sensor S2 of the second embodiment which is shown in FIG. 6 and FIG. 7, numeral 11 is a woodceramics substrate formed into a U shape in a plan, which is formed with measuring electrodes 12 and 13 at both ends of the above-mentioned woodceramics substrate 11 and is formed with a common electrode 14 in the central region. Then, the region between the above-mentioned measuring electrode 12 of the one side of the above-mentioned woodceramics substrate 11 and the common electrode 14, in a manner similar to the first embodiment, is sealed entirely by a coating 15 of a material which does not have hygroscopic property, is set as a temperature sensor 16, and the region between the measuring electrode 13 of the other side on which the coating 15 is not formed and the common electrode 14, is set up as a humidity sensor 17. Lead wire is connected to each of the above-mentioned electrodes.

Figure 8:
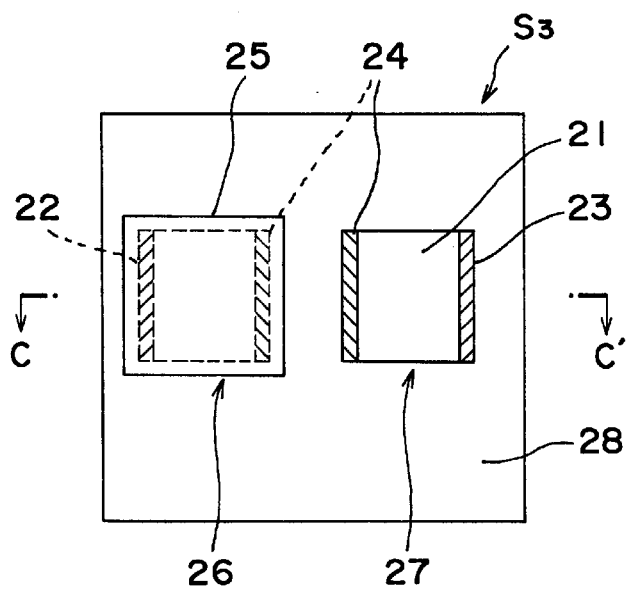
FIG. 8 is a plan view of the third embodiment of the present invention.
Figure 9:
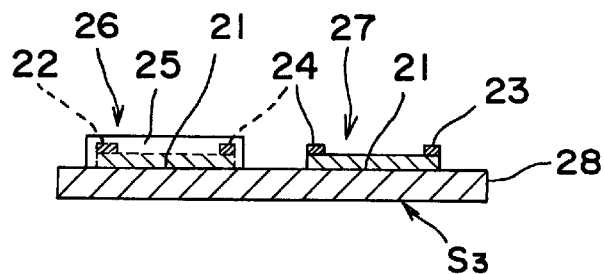
FIG. 9 is a sectional view cut along the C—C line in FIG. 8.

FIG. 8 and FIG. 9 show a humidity sensor S3 of the third embodiment of the present invention. Numeral 21 is a thin film of woodceramics which has been deposited by vacuum evaporation method, spraying method, or coating method like printing on an insulating substrate 28 (ceramics, a polymer, a cellulose, glass or the like). Here, the woodceramics thin film based on the vacuum evaporation method may be formed by the conventional methods of RF sputtering, ion-plating, ion beam deposition, thermal evaporation, and the like. In addition, it may be formed also by spraying or coating the dissolved woodceramics powder in an organic solvent, followed by drying.

Measuring electrodes 22 and 23 are formed at both ends of the above-mentioned woodceramics thin film 21, and a common electrode 24 is formed as well. The region between the measuring electrode 22 at the one side of the woodceramics thin film 21 and the common electrode 24 is sealed entirely by a nonhygroscopic thin film 25. Lead wire is connected to each of the electrodes. In the above-mentioned configuration, the side on which the nonhygroscopic thin film 25 is set as a temperature sensor 26 which conducts the temperature correction without being affected by the humidity, and the region between the measuring electrode 23 without the film coating 25 and the common electrode 24 is set as a humidity sensor 27. As for the above-mentioned woodceramics thin film 21, by utilizing an insulating substrate 28 of plastic, glass, ceramics, and the like(insulators), thin plate cut out from woodceramics bulk can also be used.

In any one of said embodiments, the temperature sensors 6, 16, and 26 are sealed by coatings 5, 15, and 25 which cut off humidity. Consequently, since there is no effect due to humidity, it is possible to obtain relative humidity by measuring the changes in electrical resistance using the temperature sensors 6, 16, and 26, and by correcting the electrical resistance values of the humidity sensors 7, 17 and 27, so that accurate humidity can be known. Furthermore, although the humidity sensor and the temperature sensor for temperature correction of the humidity sensor may be separated and each individually formed, as in the third embodiment, the manufacturing process can be simplified by setting up half of a single woodceramics substrate as the humidity sensor and making the other half the temperature sensor for temperature correction as in the first and second embodiments.

Figure 10:
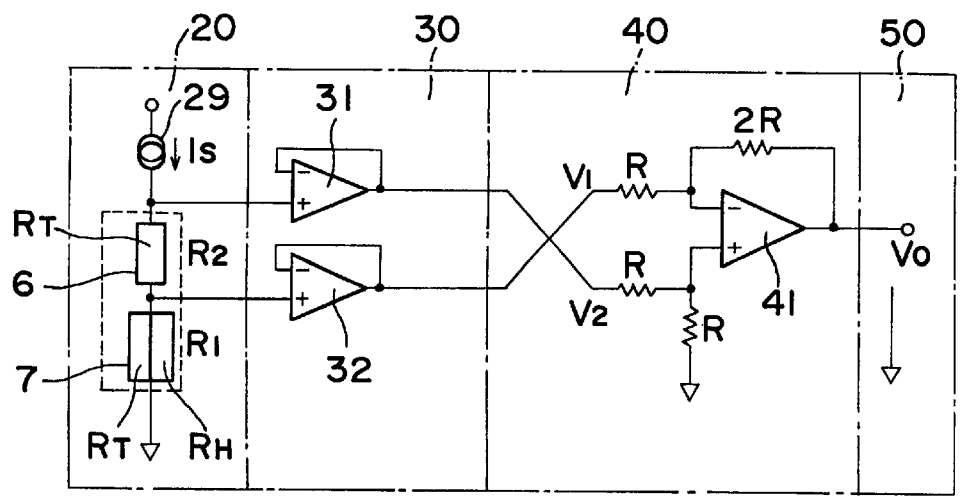
FIG. 10 is an analogue circuit diagram in the present invention.

An example of a circuit diagram of the above-mentioned humidity sensor will be explained with reference to FIG. 10. FIG. 10 is a typical example of an analog circuit and provides an output voltage which is proportional to the relative humidity (% RH). The outputs of the temperature sensor 6 and the humidity sensor 7 in a sensor drive circuit 20 are input into operational amplifiers 31 and 32 in a buffer circuit 30. After the temperature correction has been made in a differential amplifier circuit 40, it is output as a relative humidity signal in an output circuit 50 which has been differentially amplified.

More specifically, in the sensor drive circuit 20, numeral 29 is a constant current source. Since the temperature sensor 6 and the humidity sensor 7 are electrically connected in series, by applying a constant current IS of a few mAs using the constant current source 29, a potential difference of IS×R1=E1 is generated at the humidity sensor 7, and a potential difference of IS×R2=E2 is generated at the temperature sensor 6. Therefore, by differentially amplifying, IS·R2−IS·R1=Is·RH=E2−E1 is obtained; this E2−E1 results in the output which is proportional to the humidity. In order to realize E2−E1 with a simplest single-power supply circuit, a circuit which becomes V2−2V1 is to be employed. Computation (V2−2V1) is executed by the differential amplifier circuit 40, later described, which performs the subtraction. Here, RT in the sensor drive circuit 20, is the temperature contribution part due to the change in resistance, RH is the contribution part due to humidity of the change in resistance, and either of them is of negative resistance characteristics.

The buffer circuit 30 is an impedance conversion circuit of amplification magnitude 1, based on the typical operational amplifiers 31 and 32. The purpose of providing the above-mentioned buffer circuit 30 is to avoid the lowering of precision of the differential amplifier circuit 40 resulting from the difference in signal source resistances of V1 and V2. The differential amplifier circuit 40 is a differential input-type subtraction circuit based on a typical operational amplifier 41. In this circuit, since the feedback resistance of the inverted input side is 2R, V0=V2−2V1 is obtained, and an output voltage proportional to the relative humidity is obtained. Here, for example, in the case of the humidity being 0% RH, since both R2 and R1 are only of temperature contribution parts, R2=R1 is self-evident. In this case, E2=E1, i.e., V2−2V1=0, so that the output V0=0 and corresponds to the humidity 0% RH. In the case of the humidity being 100% RH, R1=min (since woodceramics has the characteristics of negative resistance), i.e., E1=min, V2−2V1min=V0max is obtained.

Accordingly, the output V0 becomes a maximum output, corresponding to the humidity of 100% RH. As a result of this, the output of an arbitrary humidity between 0 to 100% RH can be the outputs, each of which is proportional to the humidity. By inputting this output into an analog comparator circuit, an ON/OFF output corresponding to the threshold value set up beforehand can be obtained, so that binary control of the humidity can be made by this output. Also, humidity can be read by an analog display and digital display. Furthermore, by digitizing the value of this output by means of the A/D converter, it is also possible to apply it to control by computer and so forth. Moreover, it is possible to omit the buffer circuit 30 appropriately, according to the values of R1 and R2. Also when the sensor is pulse driven, rather than by direct current, in consideration of saving for the battery, by providing a rectifying circuit between the buffer circuit 30 and the differential amplifier circuit 40, the above-mentioned circuit can be used as it is.

Figure 11:
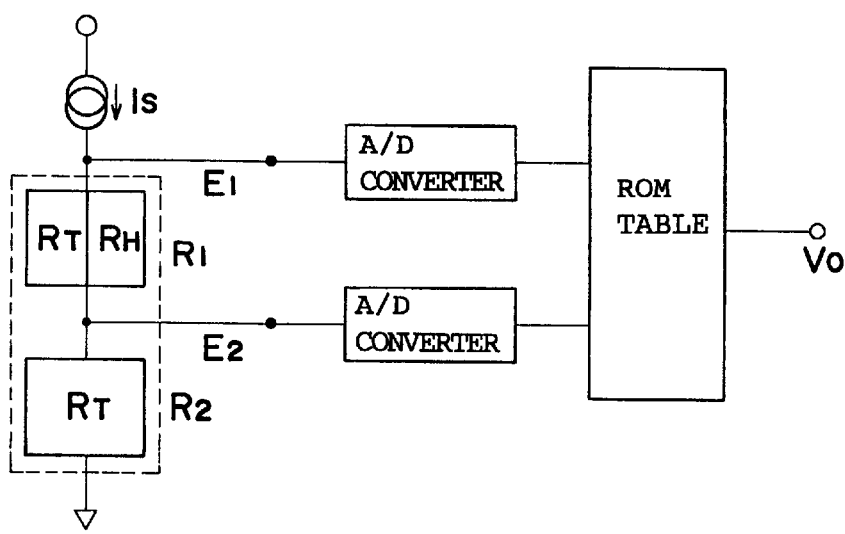
FIG. 11 is a digital circuit diagram in the present invention.

FIG. 11 shows an example of a digital circuit of the above-mentioned humidity sensor. Since ICs are becoming obtainable at very low prices in the recent years, the analog circuit of FIG. 10 can be replaced to detect humidity by using the digital circuit of FIG. 11 also. The potential difference E1 which the above-mentioned humidity sensors 7, 17, and 27 generate and the potential difference E2 which the temperature sensors 6, 16, and 26 generate, are respectively A/D converted, input into a ROM table or a one-board microcomputer, and the like. After being compared with the data stored in advance and corrected as temperature correction, the potential differences produce the output of the relative humidity.

According to the humidity sensor regarding the present invention, woodceramics only having linear characteristics with humidity are used, and a structure insensitive to humidity obtained by sealing the surface thereof is utilized as a temperature sensor for temperature correction. Note that woodceramics having the identical temperature coefficient are used for the temperature correction. In consequence, the woodceramics humidity sensor permits measuring a humidity with a high precision and a high reliability in a wide range. Furthermore, according to the present invention, woodceramics humidity sensor is low in price, small in size, and excellent in both reliability and mass-production. In addition, by having the temperature correction performed with woodceramics of identical material, temperature coefficients thereof are made to be identical, thereby substantially simplifying the circuit with high accuracy. Furthermore, since the present invention is of an electrical resistance type which employs woodceramics having moderate resistance (i.e., it is not insulator), current can be passed through the body itself, thereby making heat cleaning possible. Consequently, it will not become moldy unlike the other humidity sensor elements, such as polymers, cellulose, ceramics, and hair.

What is claimed is:

1. An electrical resistance type humidity sensor which comprises a humidity sensor in which electrodes are formed on a first woodceramics substrate, and a temperature sensor for temperature correction in which electrodes are formed on a second woodceramics substrate having the same temperature coefficient as the first woodceramics substrate and a film coating of a nonhygroscopic material is formed on the surface of the second substrate, wherein woodceramics are porous carbon material produced by sintering and carbonizing a composite material of woody material, wherein the woody material is selected from the group consisting of lumber, wood, board, paper, bamboo, wood wastes and waste papers, and a thermosetting resin at a high temperature; a resistance value measured by the humidity sensor being corrected on the basis of a resistance value measured by the temperature sensor having the identical temperature coefficient as in the woodceramics humidity sensor to obtain an output voltage in proportion to a relative humidity.

2. The electrical resistance type humidity sensor according to claim 1 wherein electrodes are formed at both ends and the center of one woodceramics substrate; a film coating of a nonhygroscopic material is formed on the surface between the electrode at one end and the electrode at the center; a film-free portion between the electrode at the other end and the electrode at the center functions as a humidity sensor; and a portion having the film coating functions as a temperature sensor for temperature correction.

3. The electrical resistance type humidity sensor according to claim 2 wherein one woodceramics substrate is formed in a line-shaped form.

4. The electrical resistance type humidity sensor according to claim 2 wherein one woodceramics substrate is formed in a U-shaped form.

5. An electrical resistance type humidity sensor wherein two separated thin plates or thin films of woodceramics are formed on one insulating substrate, wherein the woodceramics have the same temperature coefficients a film coating of a nonhygroscopic material is formed on the first thin plate or film of woodceramics to provide a temperature sensor for temperature correction; no film coating is formed on the second thin plate or film of woodceramics to provide a humidity sensor; each of the temperature sensor and humidity sensor has two electrodes, and a resistance value measured by the humidity sensor is corrected on the basis of a resistance value measured by the temperature sensor to obtain an output voltage in proportion to a relative humidity, wherein woodceramics are porous carbon material produced by sintering and carbonizing a composite material of woody material, wherein the woody material is selected from the group consisting of lumber, wood, board, paper, bamboo, wood wastes and waste papers, and a thermosetting resin at a high temperature.

* * * * *